(12) United States Patent
Faehl et al.

(10) Patent No.: US 6,245,327 B1
(45) Date of Patent: *Jun. 12, 2001

(54) BAIT FOR CONTROLLING CARPENTER ANTS

(75) Inventors: Larry G. Faehl, Cranbury; James B. Ballard, Medford, both of NJ (US)

(73) Assignee: FMC Corporation, Philadelphia, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/622,481

(22) Filed: Mar. 25, 1996

(51) Int. Cl.[7] .......................... A01N 25/00; A01N 25/02; A01N 25/24; A01N 41/06
(52) U.S. Cl. .......................... 424/84; 424/405; 424/407; 424/409; 424/659; 424/195.1; 514/406; 514/594; 514/601; 514/639; 426/1
(58) Field of Search .............. 424/84, 405, 407, 424/409, 195.1, 659; 514/601, 406, 594, 639

(56) References Cited

U.S. PATENT DOCUMENTS

| | | | |
|---|---|---|---|
| 3,220,921 | * 11/1965 | Greenbaum et al. | 514/755 |
| 3,962,461 | 6/1976 | Brown, Jr. et al. | 514/755 |
| 4,921,696 | 5/1990 | Vander Meer | 424/84 |
| 4,990,514 | * 2/1991 | Bruey | 514/275 |
| 5,928,634 | * 7/1999 | Vick et al. | 424/84 |

FOREIGN PATENT DOCUMENTS

| | | |
|---|---|---|
| 0 295 442 A2 | 5/1988 | (EP) . |
| 2 231 798 | 11/1990 | (GB) . |
| 61-025431 | 2/1986 | (JP) . |
| WO 91/07972 | 6/1991 | (WO) . |

OTHER PUBLICATIONS

Derwent abstract 89–204057/28; JP–304142; "Poison bait tablets . . ." (1989).
Derwent abstract 91–036522/05; WO 9100–007–A; "Insect bait contg. toxic insecticide . . ." (1991).
Derwent abstract 92–343785/42; "Ants inhibiting gel composn . . ."0 (1992).
Derwent abstract 92–356748/43; US Patent 5,152,096; "Pesticidal device . . ." (1992).
Derwent abstract 94–196961/24; JP 06135809; "Stomach poison agent for ants . . ." (1994).
Derwent abstract 92–247573/30; JP 92039298–B; "Killing harmful insects . . ." (1992).

* cited by examiner

*Primary Examiner*—John Pak
(74) *Attorney, Agent, or Firm*—FMC Corporation

(57) ABSTRACT

The present invention relates to an ant or yellow jacket bait that is particularly effective for controlling carpenter ants. The bait is comprised mostly of sugars in a viscous and fluid form that may be readily dispeised into an ant station at room temperatures, and provides a moist, sweet surface that is attractive to ants.

1 Claim, 1 Drawing Sheet

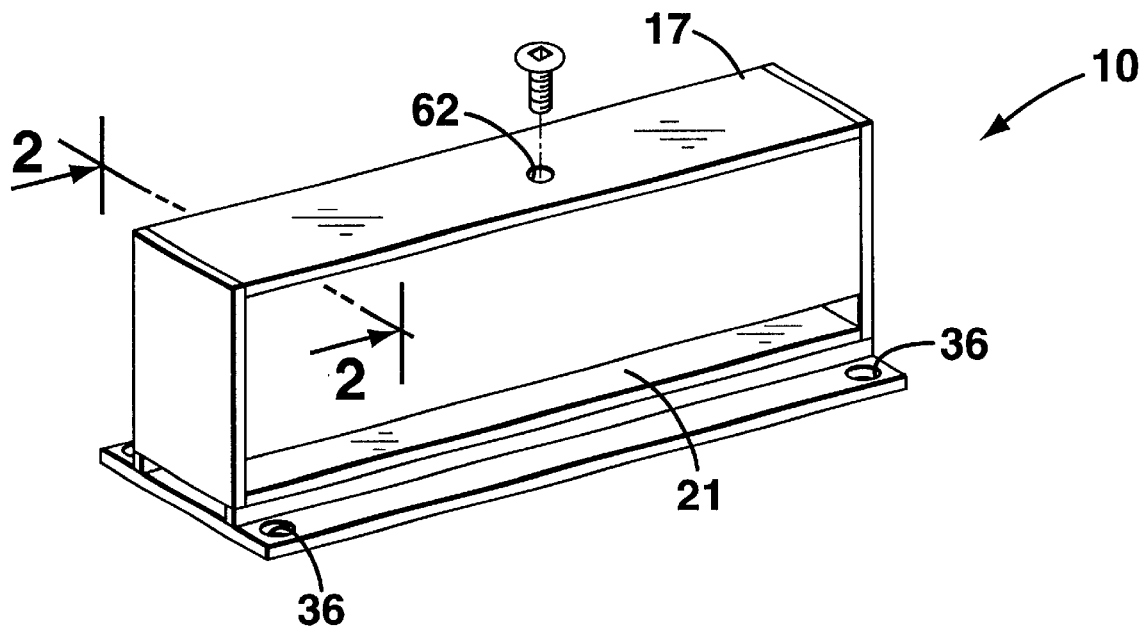
FIG_1
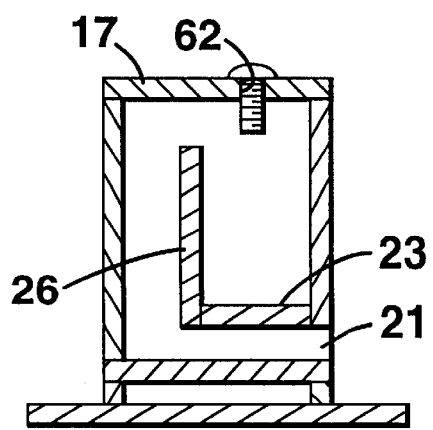
FIG_2

BAIT FOR CONTROLLING CARPENTER ANTS

BACKGROUND ART

Ants belonging to species of Camponotus, commonly known as carpenter ants, are an important economic pest. They cause structural damage to homes, telephone poles, and trees by tunneling into the wood. Methods to control carpenter ants have been evaluated based on effectiveness against the ants, environmental safety and ease of use, especially for pest control operators (PCO's) concerned with ant population management. Carpenter ants have been controlled in the field by use of sprays or dusts, methods that are considered by many to be environmentally unfriendly. Furthermore, exposure of the spray or dust to environmental elements may limit the effectiveness of the toxicant, for example, by rain washing it away. A "cleaner," more effective method of control is to place a toxic bait in an ant station so as to prevent exposure to non-target organisms, such as children and pets, and to shield the bait from environmental factors that may cause degradation and dilution of the toxicant. While non-particulate solid baits are potentially safer than liquids, powders or granular materials, they generally are not suitable for use in rebaitable, semi-enclosed ant stations. Typically, when such solid baits have been depleted, the entire self-contained station must be replaced. Preferred toxicants are ones that are slow enough acting to allow the ant time to bring it back to the nest a rid thereby deliver the toxicant to the rest of the colony.

Ants are selective in their preference for baits. What one species of ant finds appealing, another species may ignore. It is known that carpenter ants are particularly selective, but they may be attracted to baits that are moist and sweet. U.S. Pat. No. 3,962,461 describes honey and the insecticide Mirex in a liquid bait. The utility of this bait is limited by the need for an organic solvent to help solubilize Mirex and by its form as a liquid. Only a limited amount of solvent may be used before the carpenter ants are repelled, and as a liquid the bait is unsafe to children and pets.

Described in European Patent No. 0295 442 is a solid, non-particulate bait. This bait comprises the liquid sugars corn syrup and molasses, ground protein, and a polymeric binder. The polymeric binder is disclosed as conferring good coherency to the composition, thus providing a solid form that is safer in a household environment than liquids, powders or granular materials. The effectiveness of ground protein as an added feeding attractant depends on the time of season. Early in the season carpenter ants seek a mixture of sugar and protein; later they become more satisfied with food that consists entirely of sugars. Examples of ground protein having utility in baits include dried fish meal and silkworm pupae (EPO 295 442).

WO91/07972 describes an aqueous gel bait containing carrageenan which is reported to be an effective gelling agent. Such aqueous gels have an advantage over other bait forms in that they are pourable, albeit at temperatures above 60° C. With a pourable bait, a pest control professional may prepare the bait station for either indoor or outdoor ant control. However, the need to heat the bait in order to make it pourable is an obvious limitation since the bait cannot be readily dispensed at room temperature.

A suitable toxicant is one that is both toxic to the ant at low concentrations and slow acting so that the ant will distribute the toxicant to others in the colony. Examples of toxicants reported to have utility in ant baits include fluorinated sulfonamides such as sulfluramid, $C_8H_{17}SO_2NHC_2H$, (U.S. Pat. No. 4,921,696); boric acid (WO 91/07972); vyrazolines (U.S. Pat. No. 5,196,408); diflubenzuron, a chitin synthesis inhibitor (JO 1224-307); and certain hydrazones (U.S. Pat. No. 4,087,525).

It is an object of this invention to provide a highly effective carpenter ant bait that may be dispensed into an ant station at room temperature. It is a further object of this invention to provide a bait formulation that consists almost entirely of sugars so as to have both a moist, sweet surface attractive to the ants and physical properties that yield a viscous and fluid bait that may be readily used by a pest control operator in baiting an ant station.

SUMMARY OF THE INVENTION

A highly effective carpenter ant bait that may be dispensed into an ant station at room temperature is described. The bait formulation consists almost entirely of sugar substances so as to have both a moist and sweet surface attractive to the ants and physical properties that yield a viscous fluid bait that may be readily used by a pest control operator in baiting an ant station. The bait is comprised of honey, at least one liquid sugar, at least one solid sugar, and a slow-acting toxicant. Examples of liquid sugars that may be used in the present invention include light and dark corn syrup and molasses; examples of solid sugars include sucrose, melizitose, and trehalose; and examples of slow-acting toxicants effective against carpenter ants are sulfluramid and insect growth regulators. The present baits provide season-long control of carpenter ants and other ant pests without the need for added protein. A bitter agent or misfeeding inhibitor may be added to the bait of this invention to prevent accidental ingestion by pets and children. In a suitably designed ant station, the bait may be used safely indoors and outdoors with high efficacy.

BRIEF DESCRIPTION OF THE DRAWINGS

FIG. 1 is a perspective view of an apparaus that uses the invention.

FIG. 2 is a cross sectional view of the apparatus shown in FIG. 1.

DISCLOSURE OF THE INVENTION

Described herein is a bait for controlling carpenter ants comprising a mixture of sugars and a slow acting toxicant. The bait has a moist, sweet surface that is appealing to the ant. It is easily formulated to provide a fluid and viscous composition that minimizes environmental contamination caused by leakage or crumbling, but allows a PCO to readily dispense the bait into an ant station as needed. An important feature of this invention is that the bait may be injected to refill or service the ant station at room or ambient temperatures. It is most useful when dispensed into a station designed to prevent leakage, but allow for easy filling such as the clear plastic ant station described below.

The invention is exemplified using the known insecticide sulfluramid (N-ethyl-perfluorooctane-1-sulfonamide); however, other toxicants that are effective against carpenter ants may be used with this bait and are contemplated to be within the scope of this invention. These other toxicants include boric acid, pyrazolines, benzoylphenylureas such as diflubenzuron, and certain hydrazones. The insecticide-containing bait is effective in eliminating at least two species of carpenter ants: *C. pennsylvanicus* and *C. ferrugineus*. It is also effective against the following ant pests: Crematogaster sp. (acrobat ant),. Dorymyrmex sp. (pyramid ant), *Lasius*

*alienus* (cornfield ant), *Monomorium minimum* (little black ant), Pheidole sp. (big-headed ant), *Prenolepis imparis* (small honey ant), *Solenopsis molesta* (thief ant), Tapinoma sp. (odorous house ant), and *Tetramorium caespitum* (pavement ant). The bait has also been found to be effective against yellow jackets.

The term "sweet" is commonly used to describe a taste sensation caused by food having a high sugar content. Without implying or describing what sensation the ant actually experiences, as used herein "sweet" refers to a formulation or surface thereon which may be characterized as having a high sugar content that is attractive to the ant.

The bait formulations contain honey, a liquid sugar such as light corn syrup, dark corn syrup or molasses and a solid sugar such as sucrose, trehalose, or melizitose. Since light corn syrup has a high fructose content, it is believed that other high fructose syrups would be effective in these formulations. Honey may be present in concentrations of 5–40% with a preferred range of 5–15%. The remaining sugars may be present in combined concentrations of 60–95% with a preferred range of 80–90%. A preferred bait formulation contains approximately 47–50% by weight light corn syrup, 10% by weight honey, 39–43% by weight sucrose, and 0–5% by weight toxicant. The carpenter ant finds these sugary mixtures highly desirable because they offer a moist and sweet surface.

Formulations should be sufficiently wet and hygroscopic so that a dry skin does not form on the surface. When a dry skin is present, the carpenter ant will simply walk over and not be arrested by the bait. The ability to maintain a moist surface is dependent on both the hygroscopicity of the formulation and the relative humidity in the atmosphere. It is an advantage that formulations of the present invention provide a moist surface under conditions of varying humidity. It is a further advantage that the bait is fluid enough to be readily dispised into an ant station at room temperatures, but sticky and viscous enough to minimize leakage.

During the preparation of these bait formulations, the mixture of ingredients is heated to obtain a uniform or homogeneous composition. Sulfluramid which is a solid may be added either as a fine powder or as a solution in acetone. Homogeneity is best achieved when mixing is performed above 75° C. However, at higher temperatures open vessel mixing may cause loss of fluidity due to water evaporation. When too much water is lost during mixing, a composition is obtained which is difficult to dispense and is prone to forming a dry skin on its surface. For open vessel mixing, a temperature of around 50° C. provides an optimum composition with regard to both flow and homogeneity.

The bait formulation may have a viscosity between 5,000 cps at room temperature and 100,000 cps when measured at 30–35° C. A preferred viscosity is between 30,000 and 60,000 cps at 30–35° C. The viscosity may be adjusted by altering the ratio of solid to liquid sugars. Increased viscosity results from increasing the concentration of solid sugars in the formulation.

The present bait may optionally contain a number of additives. It is notable that this bait does not require added protein to attract carpenter aniis throughout the season. The bait is highly effective in the spring when carpenter ants normally prefer mixtures of proteins and sugars. Thickeners such as guar gum or carrageenan may be added, but they are not required since a solid sugar such as sucrose in the basic formulation will thicken the bait. Bitrex, an ammonium benzoate sold by Macfarlan Smith Ltd., Edinburgh, Scotland is a bitter agent that is useful in preventing accidental ingestion of the bait by non-target organisms such as pets and children.

A preferred ant bait station 10 is shown in FIGS. 1 and 2. The station is rectangular and made of clear plastic. Bait is dispensed into the station through a small opening 62 in a top wall 17.

Perpendicular inner walls 23 and 26 form compartments designed to hold liquid or gel baits in a manner that prevents loss of bait due to spillage. A slot 21 is wide enough to allow the ants ready ingress and egress, but is narrow enough to deny entry to larger species. Screw holes 36 are provided to allow the station to be mounted onto a surface such as a tree. The station is suitable for both indoor and outdoor use. To attract yellow jackets, a similar station may be used that is made of a transparent yellow plastic.

EXAMPLES 1–4

Preparation of Bait Formulations

Karo® syrup, honey, and sucrose were vigorously mixed by hand at 40° C. untfil the mixture became uniform. For formulations containing sulfluramid, an appropriate amount was added as a solution in 3.0 mL, acetone while maintaining vigorous stirring and heating. The warm mixture was injected via syringe into an ant bait station. These compositions are shown in Table 1.

TABLE 1

Bait Formulations for Examples 1–4

| Ingredient | Formulation | | | |
|---|---|---|---|---|
| | 1 | 2 | 3 | 4 |
| | Weight Percent | | | |
| Sulfluramid[a] | 0.0 | 0.5 | 0.0 | 0.5 |
| Karo ® Syrup[b] | 50.0 | 50.0 | 47.5 | 47.5 |
| Honey[c] | 10.0 | 10.0 | 10.0 | 10.0 |
| Sucrose[d] | 40.0 | 39.5 | 42.5 | 42.0 |

[a]N-Ethylperfluoro-octane-1-sulfonamide from Griffin Corporation.
[b]Light corn syrup from Best Foods Div., CPC International Inc., Englewood Cliffs, NJ
[c]Pure Grade A honey
[d]10X confectioners cane sugar from Americas Choice, Montvaille, NJ

Test Methods

Formulations 1–4 were tested as baits against four carpenter ant colonies A-D (New Jersey). Colony A was a parent colony nesting in railroad ties surrounded by oak trees and ivy. Colonies B, C and D were satellite colonies nesting in oak trees, separated from each other by about 100 yards and from colony A by more than 100 yards. Foraging trails from each of the colonies were identified, and reference points on a foraging trail from each colony were used to record the activity of ants in response to the bait. The baits were introduced by placing carcte containing 1 mL of formulation alongside the foraging trails at the base of the trees for colonies B–D and one foot from the entrance to the nest area of colony A. Activity was observed to determine ant preference for the formulations.

For the sulfluramid-containing formulations 2 and 4, fresh bait was introduced daily until the colony was eliminated (no ants passing the reference point and the entire bait remaining). The number of ants passing the reference point was recorded at the following times: (a) prior to replenishing the bait, (b) within five minutes of replenishing the bait and (c) within 15 minutes. These latter times correspond to when recruitment of ants to the bait began (five minutes after replenishing) and when the number of ants at each bait was relatively constant (15 minutes). Activity was observed to determine the effectiveness of 2 and 4 in eliminating the colonies.

Results

Formulations 1–4 were equally effective in attracting carpenter ants with no preference shown for any of the formulations. During these trials thief ants also found the baits highly attractive, and the carpenter ants exerted a great deal of effort keeping the thief ants away. Within two days the thief ants disappeared and never returned.

Formulations 2 and 4 were effective in eliminating carpenter ants. The amount of activity on the foraging trails remained relatively constant throughout the testing, and activity did not decrease until the colony was eliminated. These data are shown in Table 2. The amount of time required to eliminate a carpenter ant colony varied with the size of the colony and not with the amount of bait administered daily (1 mL/day). It took four days to eliminate the satellite colonies B–D and nine days to eliminate the larger parent colony A.

TABLE 2

Activity of Formulations 2 and 4 Against Carpenter Ants

| | | | # Carpenter Ants Passing Ref. Prior to | | |
|---|---|---|---|---|---|
| Formulation | Colony | Day | Replenishing Bait | 5 min. | 15 min. |
| 2 | A | 0 | 18 | 6 | 18 |
| | | 1 | 14 | 4 | 23 |
| | | 2 | 19 | 7 | 21 |
| | | 3 | 11 | 6 | 19 |
| | | 4 | 23 | 8 | 20 |
| | | 5 | 9 | 3 | 22 |
| | | 6 | 14 | 5 | 17 |
| | | 7 | 10 | 3 | 24 |
| | | 8 | 7 | 4 | 17 |
| | | 9 | 9 | 4 | 11 |
| | | 10 | 0* | 0* | 0* |
| | | 30 | 0* | 0* | 0* |
| 2 | B | 0 | 11 | 4 | 17 |
| | | 1 | 8 | 3 | 19 |
| | | 2 | 7 | 5 | 14 |
| | | 3 | 5 | 3 | 9 |
| | | 4 | 0* | 0* | 0* |
| | | 30 | 0* | 0* | 0* |
| 4 | C | 0 | 8 | 5 | 14 |
| | | 1 | 6 | 4 | 16 |
| | | 2 | 11 | 4 | 19 |
| | | 3 | 7 | 3 | 9 |
| | | 4 | 0* | 0* | 0* |
| | | 30 | 0* | 0* | 0* |
| 4 | D | 0 | 14 | 3 | 21 |
| | | 1 | 12 | 4 | 16 |
| | | 2 | 17 | 5 | 17 |
| | | 3 | 9 | 2 | 15 |
| | | 4 | 1 | 0* | 0* |
| | | 5–30 | 0* | 0* | 0* |

* Colony eliminated.

EXAMPLES 5–7

Preparation of Bait Formulation

A mixture of Karo® syrup, honey, and sucrose was heated to about 50° C. and vigorously mixed in a Kitchen Aid heavy duty mixer until the mixture became uniform. In formulation 6, Bitrex was also added to the mixture. Sulfluramid was added as a 1:1 solution in acetone. Upon completion of addition and while maintaining the temperature at about 50° C., the entire formulation was vigorously mixed until the mixture became uniform. The warm mixture was injected via syringe into a bait station, either of the type shown in FIG. 1 or an empty FluorGuard™ Ant Control Bait station. Formulation 7 was prepared as described above except that the mixture was heated to 75° C. After injection of 7 into an empty FluorGuard™ station, a sponge was placed inside the station, and the station was then heated in a microwave oven to allow the sponge to absorb the bait. These baits are shown in Table 3.

TABLE 3

Bait Formulations for Examples 5–7

| | Weight in Grams (wt. %) | | | | |
|---|---|---|---|---|---|
| Formulation | Sulfluramid[a] | Karo | Honey[c] | Sucrose[d] | Bitrex[e] |
| 5 | 10.0 (0.5) | 950.0 | 200.0 | 840.0 | |
| 6 | 7.0 (0.5) | 664.9 | 140.0 | 588.0 | 0.1 (0.01) |
| 7 | 1.5 (0.5) | 147.5 | 30.0 | 126.0 | |

[a-d]as described in Table 1.
[e]Bitrex is an ammonium benzoate from Macfarlan Smith Ltd., Edinburgh, Scotland, is a bitter agent that deters accidental ingestion.

Test Methods

Formulations 5–7 in FluorGuard™ stations were tested as baits against eight carpenter ant colonies (E–L, with colony G being the largest) against two species of carpenter ants: *C. pennsylvanicus* and *C. ferrugineus* (New Jersey). The baits for formulations 5 and 6 were prepared by dispensing ten mL of the corresponding formulation into separate ant stations. For formulation 7, two mL were dispensed into the bait station.

A reference point on a foraging trail for each colony was identified and used in recording the activity of the carpenter ants in response to the bait. The number of ants passing the reference point were recorded at different times of the day to coincide with maximum activity periods based on weather conditions. To establish a baseline for trail activity, colonies were not baited for the first three days. On the fourth day, the eight colonies were baited as follows:

Colony E: six ant bait stations containing formulation 7 placed on the same side of the foraging trail;

Colonies F, G, I, and J: three stations containing formulation 5 and three stations containing formulation 6 all placed on the same side of the foraging trail. Stations containing 5 were replenished on the sixth day for colony G and on the ninth day for colony I.

Colony H: two stations containing formulation 5 on one side of the foraging trail and two stations containing formulation 6 on the other side of the trail.

Colonies K and L: control stations that were not baited.

Results

Formulations 5–7 were all effective in eliminating both the *C. pennsylvanicus* and *C. ferrugineus* carpenter ants (Table 4). None of the six baited colonies showed activity by day 9 (the fifth day following baiting). For the control colonies activity on the foraging trails remained relatively constant throughout the test with variations attributable to weather changes. These results are shown in Table 5. Thief and/or pavement ants found the baits attractive. Pavement ants in particular deter the carpenter ants from accepting the bait. Where this was a problem (colony I), rebaiting after the pavement ants were eliminated then eliminated the carpenter ants. Approximately 30 mL of bait is typically sufficient to eliminate a carpenter ant colony, though more may be required for larger colonies such as G.

TABLE 4

Activity of Formulations 5–7 Against Carpenter Ants

| Formulation | Species | Colony | Day | # Ants Passing Ref. Pt. |
|---|---|---|---|---|
| 7 | CP** | E | 1 | 6 |
| | | | 2 | 9 |
| | | | 3 | 10 |
| | | | 4 | 11 |
| | | | 5 | 8 |
| | | | 6 | 12 |
| | | | 7 | 5 |
| | | | 8 | 0 |
| | | | 9 | 1 |
| | | | 10–14 | 0* |
| 5 | CF** | F | 1 | 11 |
| | | | 2 | 16 |
| | | | 3 | 12 |
| | | | 4 | 18 |
| | | | 5 | 10 |
| | | | 6 | 18 |
| | | | 7 | 12 |
| | | | 8–14 | 0* |
| 5 | CP | G | 1 | 21 |
| | | | 2 | 18 |
| | | | 3 | 14 |
| | | | 4 | 18 |
| | | | 5 | 26 |
| | | | 6 | 14 |
| | | | 7 | 15 |
| | | | 8 | 4 |
| | | | 9 | 0 |
| | | | 10 | 2 |
| | | | 11–14 | 0* |
| 5 and 6 | CP | H | 1 | 8 |
| | | | 2 | 10 |
| | | | 3 | 6 |
| | | | 4 | 8 |
| | | | 5 | 12 |
| | | | 6 | 5 |
| | | | 7 | 1 |
| | | | 8–30 | 0* |
| 6 | CP | I | 1 | 6 |
| | | | 2 | 14 |
| | | | 3 | 11 |
| | | | 4 | 15 |
| | | | 5–8 | NC*** |
| | | | 9 | 11 |
| | | | 10 | 17 |
| | | | 11 | 2 |
| | | | 12 | 0 |
| | | | 13 | 1 |
| | | | 14 | 0* |
| 6 | CP | J | 1 | 17 |
| | | | 2 | 15 |
| | | | 3 | 21 |
| | | | 4 | 16 |
| | | | 5 | 22 |
| | | | 6 | 14 |
| | | | 7 | 6 |
| | | | 8 | 0 |
| | | | 9 | 2 |
| | | | 10–30 | 0* |
| Control Colony | CP | K | 1 | 14 |
| | | | 2–13 | 5–23 (avg 14) |
| | | | 14 | 12 |
| Control Colony | CP | L | 1 | 9 |
| | | | 2–13 | 6–18 (avg. 12) |
| | | | 14 | 13 |

**CP refers to *C. pennsylvanicus* and CF refers to *C. ferrungineus*.
***NC indicates no count because pavement ants invaded the bait.

Formulations 5 and 6 were compared in order to determine if Bitrex had an effect on carpenter ant preference for the bait. Colonies M and N were located, and the foraging trail and corresponding reference point were identified for each colony. A bait containing 5 (no Bitrex) was placed on one side and a bait containing 6 (with Bitrex) was placed on the opposite side of each trail. The number of ants passing the reference point was recorded every five minutes during a sixty minute period. The results show that the carpenter ants preferred formulation 5 but accepted 6 if they encountered it first or if 5 was depleted (Table 5).

TABLE 5

Comparative Acceptance of Formulations 5 and 6

| | | | # Carpenter Ants Passing Ref. | |
|---|---|---|---|---|
| Minutes | Species | Colony | 5 | 6 |
| 5 | CP | M | 0 | 3 |
| 10 | | | 0 | 6 |
| 15 | | | 4 | 7 |
| 20 | | | 7 | 2 |
| 25 | | | 8 | 1 |
| 30 | | | 5 | 0 |
| 35 | | | 6 | 2 |
| 40 | | | 7 | 0 |
| 45 | | | 8 | 3 |
| 50 | | | 9 | 1 |
| 55 | | | 6 | 1 |
| 60 | | | 4 | 0 |
| 5 | CP | N | 9 | 13 |
| 10 | | | 8 | 9 |
| 15 | | | 12 | 6 |
| 20 | | | 19 | 3 |
| 25 | | | 14 | 1 |
| 30 | | | 15 | 0 |
| 35 | | | 18 | 0 |
| 40 | | | 11 (bait) | 6 |
| 45 | | | 6 | 8 |
| 50 | | | 3 | 17 |
| 55 | | | 2 | 14 |
| 60 | | | 3 | 16 |

What is claimed is:

1. A bait for controlling ants or yellow jackets, said bait comprised of a toxicant, honey, at least one liquid sugar, and at least one solid sugar, said honey present in a concentration of approximately 5–40% by weight and said sugars present in a combined concentration of approximately 60–95% by weight, wherein said toxicant, at least one liquid sugar and at least one solid sugar (i) provide a fluid, moist and viscous composition under conditions of varying humidity, (ii) are collectively wet and hygroscopic so that a dry skin does not form on the surface thereof for at least one day, and (iii) are fluid enough to be readily dispensed into a bait station but sticky and viscous enough to minimize leakage from the bait station.

* * * * *